United States Patent [19]

Callahan

[11] 4,412,533
[45] Nov. 1, 1983

[54] SLEEP-INDUCING DEVICE

[76] Inventor: Doris S. Callahan, 2712 Thomas, Fort Worth, Tex. 76117

[21] Appl. No.: 336,100

[22] Filed: Dec. 31, 1981

[51] Int. Cl.³ .............................................. A61H 1/00
[52] U.S. Cl. .......................................... 128/33; 5/109
[58] Field of Search ..................... 128/33, 1 C, 52, 51; 5/108, 109

[56] References Cited

U.S. PATENT DOCUMENTS 3,585,989  6/1971  Little .................................... 128/33
3,799,153  3/1974  Short .................................... 128/33

*Primary Examiner*—Stephen C. Pellegrino
*Attorney, Agent, or Firm*—Schwartz, Jeffery, Schwaab, Mack, Clumenthal & Koch

[57] ABSTRACT

An improved sleep-inducing device is disclosed for attachment to more than one bed of the type having a frame, a spring assembly supported by the frame and a mattress supported on the spring assembly, the device comprises: a base member; a motor mounted on said base member; means for connecting said base member to more than one bed frame; a plurality of rotatable crank disks; means driveably and adjustably coupling said motor to each of said crank disks; said crank disks having a link arm connecting each of said disks to a different spring assembly; each link arm being arranged to oscillate said spring assembly in response to the rotation of said crank disk; and means for independently varying the degree of oscillation imparted to each spring assembly to which said device is attached.

9 Claims, 6 Drawing Figures

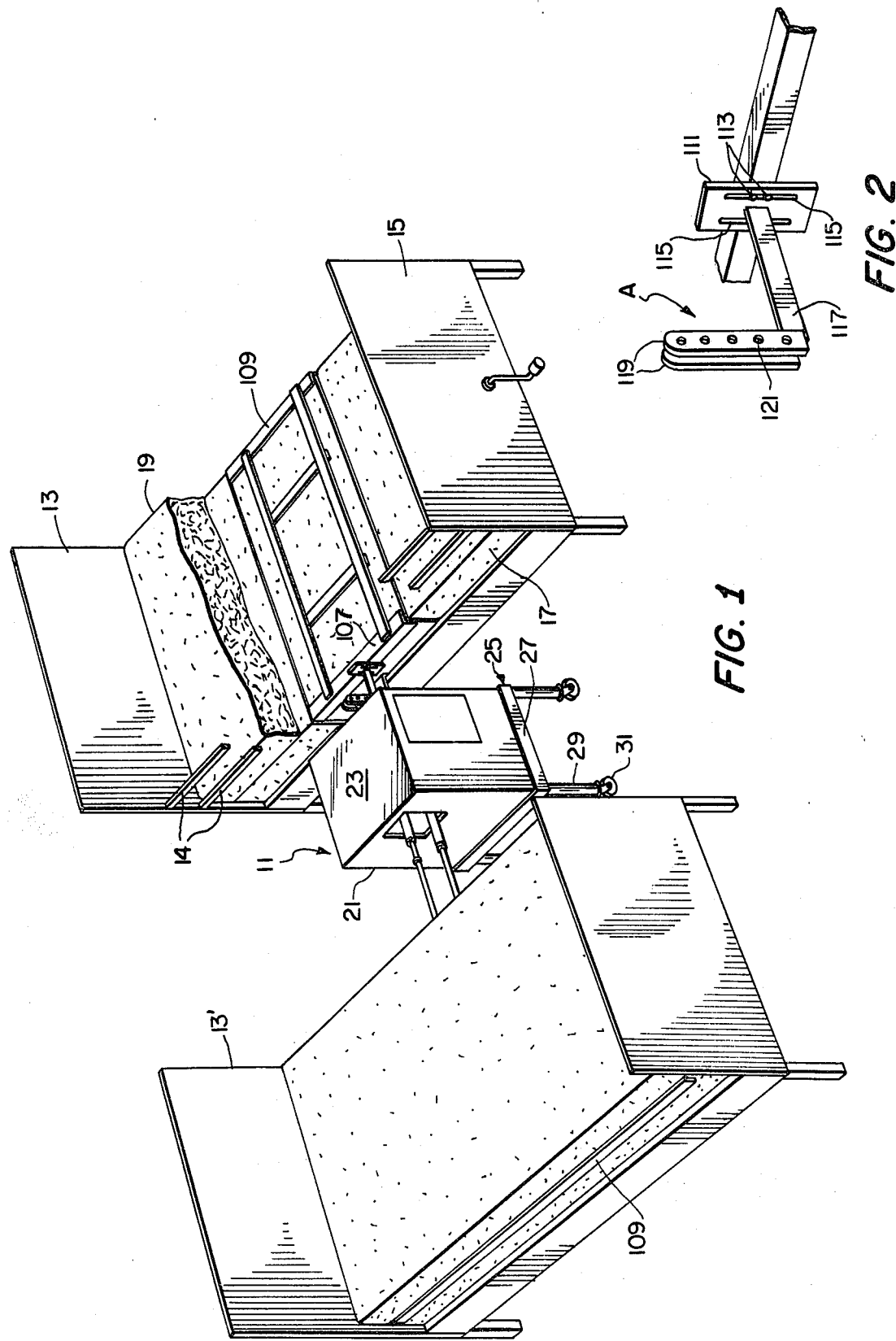

SLEEP-INDUCING DEVICE

BACKGROUND OF THE INVENTION

The present invention generally relates to a sleep-inducing device of the same general type as disclosed in my prior issuing U.S. Pat. Nos. 2,895,468 and 3,799,153, and more particularly to an improved sleep-inducing device for imparting independent oscillatory movement to more than one bed.

In order to supply the occupant of a bed with a relaxing oscillatory motion, sleep-inducing devices of the type concerned here generally employ a frame-like member which fits over the top of the spring assembly of the bed and is connected to an oscillating link arm driven by a rotating crank disk. The frequency and amplitude of the oscillatory movement imparted to the frame-like member is determined by the speed of rotation of the disk and the radial distance between the point at which the link arm is attached to the disk and the axis of rotation of the disk. Thus, a desired gentle rocking motion can be selectively provided by varying the frequency and amplitude of the oscillations imparted to the bed.

This gentle undulating movement has been found to provide a tranquilizing effect and thus can be employed in lieu of the administration of sleep-inducing medication, which is often accompanied by undesirable side effects. Accordingly, devices of this type have particular utility in the home as well as large institutes such as hospitals caring for burn patients, newborns, children, mental patients, the elderly, veterans and the like.

Known sleep-inducing devices employing oscillating link arms are operationally quite efficient, but do possess certain definite disadvantages. Heretofore, only a single bed could be attached to a device at a time, thereby requiring a separate device for each bed, a somewhat prodigal arrangement. Further, in order to vary the degree of oscillation imparted to a bed, a timely and involved procedure, involving the detachment of the link arm from the crank disk, is required. In this regard, the link arm, of the known devices, is typically connected to the disk by means of a plurality of apertures therethrough, each aperture being located at a different radial distance from the center of the disk. As a result, the variety of degrees of oscillating is limited to the number of apertures. Further, since most hospital beds include guard rails, considerable care is necessary when connecting the prior devices to a hospital bed to assure that the link arm is clear of the guard rails.

SUMMARY OF THE INVENTION

Accordingly, it is an object of the present invention to overcome the above-noted deficiencies of the known devices.

It is another object of the present invention to provide an improved sleep-inducing device which is adapted to be attached to more than one bed of virtually any size and/or design.

It is another object of the present invention to provide a sleep-inducing device adapted to continuously and selectively vary the degree of oscillation imparted to each bed by employing means for providing continuous adjustment of the radial distance between the connection point of the link arm to the disk and the center of the disk without the need for removing the link arm from the disk.

It is another object of the present invention to provide a sleep-inducing device adapted to independently vary the degree of oscillation imparted to each bed to which the device is attached.

Still another object of the present invention is to provide an improved arrangement for connecting the link arm to the movable frame-like member to more easily accommodate the presence of a guard rail and to provide improved strength and stability.

It is yet another object of the present invention to provide an improved sleep-inducing device employing an improved frame-like member adapted to further vary the modes of oscillation which can be imparted to a bed.

In accomplishing the foregoing objects, there has been provided according to the present invention an improved sleep-inducing device for attachment to more than one bed of the type having a frame, a spring assembly supported by the frame, and a mattress supported on the spring assembly. The device comprises a base member, a motor mounted on the base member, means for connecting the base member to more than one bed frame, a plurality of rotatable crank disks, apparatus for connecting the crank disk with the motor, and a link arm connecting each crank disk to a different spring assembly. The link arm is connected to the spring assembly and arranged so as to oscillate the spring assembly in response to the rotation of the crank disk. Additionally, means for independently varying the degree of oscillation imparted to each spring assembly are included. Preferably, the oscillation varying means comprises providing each crank disk with a diametric guide channel and a lockable pin member arranged to slide freely in the guide channel when the member is in an unlocked condition. The pin member is connected to a link arm by means of a rotatable bearing and includes means for locking the pin member at any selective positions along the guide channel. As a result, the present invention is adapted to selectively provide an increased variety of degrees of oscillation.

The device also comprises a generally rectangular frame-like member to which the oscillating link arm can be attached at a variety of different points so as to provide different modes of oscillation to the bed. This frame-like member is preferably adjustable in size, both longitudinally and laterally, and has downwardly depending flange portions on all four sides to engage the spring assembly.

When the device is to be employed in connection with a hospital bed, an improved adjustable means for connecting the link arm to the frame-like member is employed in order to more easily accommodate the presence of a guard rail.

Other objects, features and advantages of the present invention will become apparent from the detailed description of the invention which follows hereafter.

BRIEF DESCRIPTION OF THE DRAWINGS

In the drawings:

FIG. 1 is an external perspective view, partially cut away, of the sleep-inducing device according to the present invention illustrated in its normal operating procedure connected to beds of different designs;

FIG. 2 is a detailed view of the improved adjustable means for attaching the sleep-inducing device to a hospital bed to more easily accommodate the presence of a guard rail;

DETAILED DESCRIPTION OF THE PREFERRED EMBODIMENT

Figure 3:
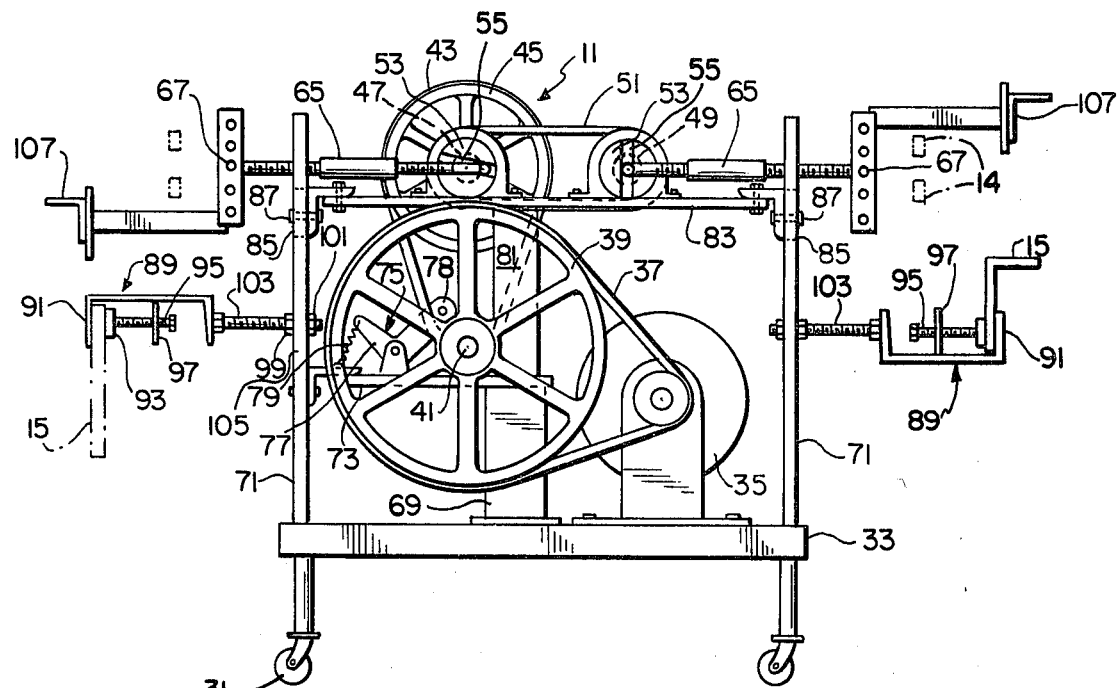
FIG. 3 is an elevational view of the device of FIG. 1 shown with the exterior cover removed.

A sleep-inducing device, generally indicated at 11, is illustrated in FIG. 1 in its normal position of attachment to a pair of beds 13 and 13', the bed 13 to the right of the device being a hospital bed having guard rails 14 and the bed 13' to the left of the device having the design of a regular bed. Each bed consisting of a frame 15 which supports a coil spring assembly 17 which, in turn, supports a mattress 19. The spring assembly 17 of the hospital bed 13 is divided into three sections which lie along the longitudinal axis of the bed 13 and which are capable of being adjusted while the spring assembly of the regular bed comprises a single member. The entire sleep-inducing device 11 is enclosed within a cabinet 21 of metal, plastic or the like, preferably containing a sound insulating lining material, with the top surface 23 of the cabinet 21 being of appropriate size and height to serve as a convenient bed-side table. The top surface preferably contains raised edges, thereby making the overall design both safe and functional. Also, the cabinet preferably has a door to provide easy access for adjusting the device. The door may include a lock to prevent unauthorized access or tampering, and the lock may include a timer to prevent access except at specific times.

In FIG. 1, because the device is depicted in use with a hospital bed, the optional feature of a separate stand 25 is employed to support the device 11 at a sufficient elevation from the floor to permit attachment to the higher than normal level of the hospital bed. The stand 25 consists of a frame 27, into which the sleep-inducing device 11 exactly fits, and four upstanding legs 29 which are provided at their lower ends with casters 31 to render the device mobile even when in the elevated position.

The hospital bed 13 is connected to the sleep-inducing device 11 by means of an improved connection arrangement generally indicated at A in FIG. 2. The improved connection arrangement A, is employed to more easily accommodate the presence of the guard rails 14 and can be inverted. The regular bed 13' is connected to the device 11 by means of a vertically adjustable plate bearing pivot bracket, generally indicated at B. The plate B is the same as that disclosed in my prior U.S. Pat. No. 3,799,153, herein incorporated by reference. Therefore, the device 11, of the present invention is adapted for use with both the previously known attachment arrangement B as well as the improved attachment arrangement A of the present invention.

In FIG. 3, the sleep-inducing device 11 is illustrated in detail showing the flat base member 33 upon which the entire device rests, the base member may include casters 31 attached to the bottom side thereof to render the device easily mobile. A variable speed motor 35 is secured to the top of the base member 33, and a small pulley on the drive shaft of the motor drives the flexible slotted belt 37 which in turn drives a large toothed pulley 39 journaled on a transverse shaft 41. At the opposite end of the shaft 41, there is journaled a small, toothed pulley (not shown) which drives a second flexible slotted belt 43 and this belt in turn drives a second large pulley 45. Pulley 45 is journaled to one end of a second transverse shaft 47 which is driveably connected to a third transverse shaft 49 by means of a flexible belt 51. It is understood by one of ordinary skill in the art that the slotted belt and tooth pulley arrangements can also take the form of any suitable drive connection arrangement such as a flexible belt having a triangular shaped cross-section and channel pulley. Attached to one end of each shaft 47, 49 is a crank disk 53 shown in detail in FIG. 4.

Figure 4:
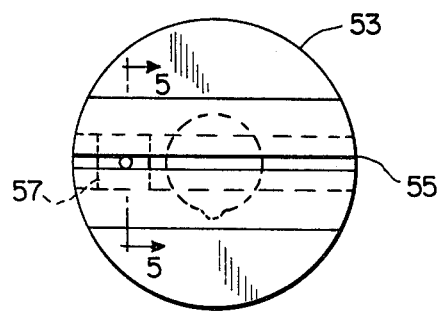
FIG. 4 is a detailed isolated view of the preferred crank disk employed in the sleep-inducing device of the present invention.
Figure 5:
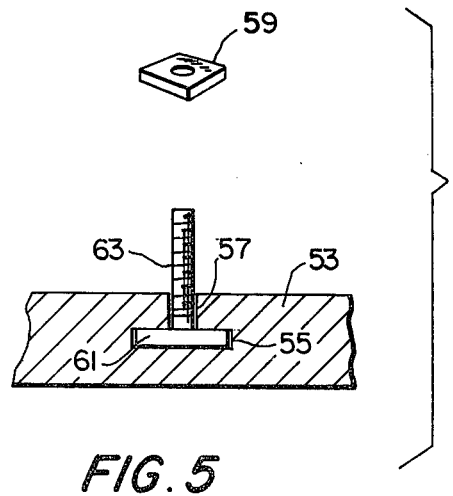
FIG. 5 is a cross-sectional view taken along the line 5—5 in FIG. 4.

Referring to FIGS. 4 and 5, the crank disk 53 includes a guide channel 55 adapted to receive a lockable sliding pin member 57, which can be unlocked and moved along the guide channel 55 when the device is stopped. The pin member 57 can be selectively located at different radial distances from the center of the crank disk 53 and locked in place by means of a locking member 59 illustrated in FIG. 5. Referring to FIG. 5, the sliding member includes an expanded head portion 61 which fits into the guide channel 55, and a threaded shank portion 63 which threadingly engages the locking member 59. The threaded shank portion 63 is designed to pivotally connect one end of a link arm 65 shown in FIG. 3 to the crank disk 53 and the locking member 59 secures the sliding member 57 at any selected radial distance from the center of the crank disk 53.

The link arm 65 can be of the type disclosed in my prior U.S. Pat. Nos. 3,799,153 or 2,895,468, herein incorporated by reference, or may take the form of a variable length shock absorber. At the proximal end of the arm 65 is formed an aperture suitably sized to accommodate the shank portion 63 of the pin member 57. A suitable bearing surface, which allows for relative rotational movement between the pin member 57 and the link arm 65, preferably engages the shank portion 63 of the pin member 57. The locking member 59 is threaded onto the shank portion 63 of the member 57 until the head portion 61 is firmly and immovably seated against the guide channel 55, the link arm being positioned between the locking member 59 and the outer surface of the crank disk 53. Due to the suitable bearing surface, the link arm 65 can freely pivot about the pin member 57 which is locked in place due to the wedging action of the tightened locking member 59. Therefore, the distance between the connection point of the link arm 65 to the rotating disk and the center of the disk can be set at any desired radial distance, thereby providing an infinite variety of degrees of oscillation.

In order to reset the radial distance between the connection point of the link arm 65 and the center of the disk 53, the locking member 59 is rotated in the opposite direction until the pin member 57 is freely slideable within the guide channel. Thereafter, the radial distance can be reset without the need for removing the link arm 65 from the crank disk 53.

Mounted in the approximate center of the base portion 33 is a hollow tubular member 69. Also mounted on and secured to the base member 33 are a pair of vertically standing bars 71. A horizontal longitudinally extending plate 73 is connected to one of the vertical bars 71 and supports the laterally extending shaft 41 by a pair of bearing brackets (not shown). Also supported on the plate 73 is a belt tightening apparatus, generally indicated at 75, consisting of a bell crank 77 carrying one end pulley 78 resting in contact with the flexible belt 43 and being spring biased at the other end by means of spring 79 attached to plate 73.

Slideably positioned inside of tubular member 69 is a second telescoping tubular member 81 which may be positioned at various heights within tubular member 69 by means of a set screw or the like as disclosed in my prior U.S. Pat. No. 3,799,153. At the top of the telescoping tubular member 81 is secured a second horizontal plate 83 which for added stability may optionally be further secured at the top portion of each vertical bar 71. The plate 83 carries the upper laterally extending shafts 47, 49 which are mounted thereon by means of bearing brackets. If the horizontal plate 83 is secured to the upper portion of each vertical bar 71, it is necessary that the securing arrangement be designed in a manner to permit vertical motion along the bar 71 in response to vertical adjustment of the telescoping members 81 and 69. This may be accomplished by providing a slot 85 in each vertical bar 71 wherein a bolt 87 or the like utilized to secure plate 83 to a bar 71 may be vertically displaced.

Each vertical bar 71 carries in its center portion a clamping device, generally indicated at 89, for connecting the base member 33 to a bed frame 15. The clamping device, shown in detail in FIG. 3, comprises a generally U-shaped member 91 normally aligned in a downwardly directed position to hook over the edge of a bed frame. The U-shaped member 91 includes a clamping vice-like member 93 having a threaded shank 95 which engages a plate 97. By rotating the threaded shaft 95, the vice-like member 93 secures the U-shaped member 91 to the bed frame 15. The U-shaped member 91 is attached to the vertically standing bar 71 by means of two nuts 99, 101 which are secured on a threaded shank 103. The threaded shank 103 is slideable within a vertically arranged slot generally indicated at 105 cut through the bar 71 in order to permit vertical adjustment of the entire clamping mechanism 89. The arrangement allows the U-shaped member 91 to be rotated 180° or more from its normally downwardly directed position about a horizontal axis. Thus, when the device 11 is used with a regular-type bed 13, the clamping mechanism 89 is fixed in its normally downwardly directed position, as illustrated in the left-hand side of FIG. 3, and clamped to the frame 15 thereby securing the device 11 to the bed 13 to hold the device 11 steady during operation. The clamping mechanism 89 is rotated to an upwardly directed position and fixed in place, as illustrated by the right-hand side of FIG. 3, for attachment to the downwardly turned sides of a hospital bed-type frame 15. The clamping mechanism is tightened until the device 11 is steady during operation, thereby preventing an undesirable wobbling movement. In this way, the sleep-inducing device can be adapted for use in connection with beds, such as hospital beds, wherein the frame design does not permit clamping of the frame from above.

Figure 6:
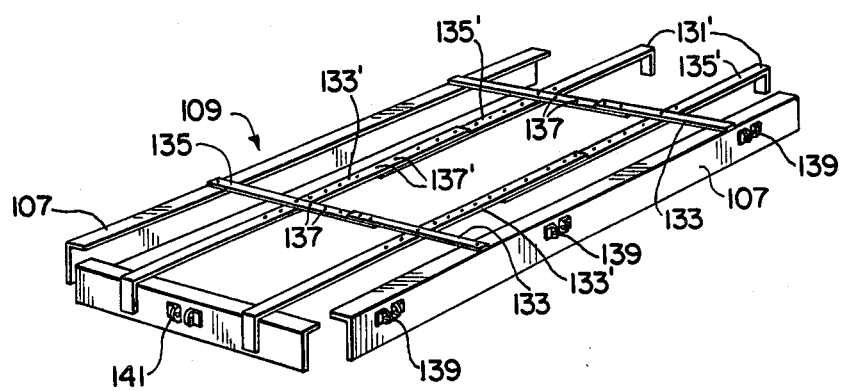
FIG. 6 is a perspective view of the improved adjustable frame of the present invention.

The distal end of each link arm 65 is pivotally connected to a side bar 107 of an adjustable frame member 109 discussed in detail in FIG. 6, which is adapted to be placed over the spring assembly of a bed between the spring 17 and the mattress 19. As illustrated in FIG. 1, the frame member 109 can be designed especially for use on the hospital bed 13 and is adapted to fit over any of the three sections of the hospital bed 13 as is desired by the user. When used in connection with the regular bed 13', the frame 109 fits over almost the entire length of the spring assembly.

A further and important feature of the invention, particularly in the embodiment where the device is used on a hospital bed, is illustrated in FIG. 2 and resides in the improved connection arrangement A for connecting the link arm 65 to the frame 109. The connection arrangement is vertically adjustable by virtue of an adjustable plate 111 adapted to accommodate bolts 113 which are slideable within vertical slots 115 in the plate 111. An extension arm 117 connects the plate 111 to a pair of support members 119 having a plurality of aligned apertures 121 therethrough. The extension arm 117 allows the device 11 to reach through the guard rails 14 of a hospital bed to the side rail 107 as illustrated by the right-hand side of FIG. 3. The apertures 121 cooperate with the retractable pins 67 of the link arms 65 to connect the link arms 65 to the members 119. As a result, the connection arrangement A can be inverted as illustrated in FIG. 3 so that the link arm 65 will not interfere with the placement of a guard rail on the bed, such as is common with hospital beds.

Referring to FIG. 6, the longitudinally and laterally adjustable frame 109 consists of longitudinally extending side bars 107, each consisting of an angular cross-section bar, with downwardly extending side flanges. Adjustable cross bars 131, 131' consist of pairs of overlapping bar segments 133, 133' and 135, 135' having spaced apertures 137, 137' respectively, which permit the bar segments to be fastened together in an overlapping relationship by bolts or the like. One or both side bars 107 can be provided with a plurality of opposing apertured pivot brackets 139, spaced along the longitudinal length of the frame 109. By attaching one end of the oscillating link arm 65 to a selected bracket, different modes of oscillatory motion can be imparted to the bed. For example, if the ink arm 65 is attached to the foot of the frame, the oscillatory motion of the link arm would be imparted to the foot of the bed, and if attached to the head of the frame, the oscillatory motion would be imparted to head of the bed. An additional pivot bracket 141 is provided at the head or foot of the frame so that a longitudinal oscillatory movement can be imparted to the bed when the link arm is suitably attached.

It will be readily understood, the device is attached to a pair of beds by suitably adjusting each frame 109 to receive the spring unit of the bed, the frame 109 being placed between the spring unit of the bed and the mattress which rests thereon, so that the spring unit is received in the enclosure defined between the depending flanges of longitudinally extending side bars 109. The device 11 is then rolled up between the pair of beds as illustrated in FIG. 1, and the height of the link arm 65 is adjusted to correspond to the level of the frame member 109 by sliding telescoping member 81 within tubular member 69 and repositioning horizontal plate 83 along each vertical bar 71. Each U-shaped bracket member 91 is then adjusted to the proper height by sliding bolt 103 within slot 105. Thereafter, each U-shaped member 91 is attached to one of the pair of beds 13 and 13'. Link arms 65 are then attached to the frame member 109 by being pivotally connected between the apertured members 119.

While the device is stopped, the sliding member 57 can be positioned at any selected radial distance from the center of the crank disk 53 and locked in place. It is understood that each sliding member 57 of each crank disk 53 can be set independently.

When the motor 35, which can be driven at variable speeds, is energized, its torque is transmitted through the respective coupling pulleys to the crank disks 53, whereupon it is then transmitted by the link arm 65 to each frame 109. It will be apparent from FIGS. 3 and 4 that the rotation of the crank disks causes each frame 109 to be oscillated in a substantially horizontal direction, providing corresponding horizontal oscillation of the mattress 19, thereby producing a gentle, sleep-inducing oscillating effect on the occupant of the bed. As a result, individuals which are bedridden do not develop bed sores and in some cases the gentle, oscillating effect promotes healing thereof. Moreover, since the oscillatory effect is generally relaxing, in institutions, such as children's hospitals, mental hospitals, and the like, the device can be used in lieu of massive doses of medication designated to tranquilize the bedridden patient.

While the improved sleep-inducing device according to the present invention has been described with reference to specific embodiments thereof, it will be appreciated that various modifications falling within the spirit of the invention will become apparent to those of ordinary skill in the art. For example, a timer may be attached to the device in order to operate it at set periods. Further, a remote switch can be attached to the device to activate the device from a bed without requiring the occupant to move. Therefore, it is intended that the scope of the present invention be limited only by the claims appended hereto.

What is claimed is:

1. A sleep-inducing device for attachment to more than one bed of the type having a frame, a spring assembly supported by the frame and a mattress supported on the spring assembly, the device comprising:
   a base member;
   a motor mounted on said base member;
   means for connecting said base member to more than one bed frame;
   a plurality of rotatable disks;
   means for driveably and adjustably coupling said motor to each of said crank disks;
   said crank disks each having a link arm connecting each of said disks to a different spring assembly;
   each link arm being arranged to oscillate said spring assembly in response to the rotation of said crank disk; and
   means for independently varying the degree of oscillation imparted to each spring assembly to which said device is attached, wherein said varying means comprises a guide channel in each of said disks and a lockable sliding pin member arranged to slide in said guide channel when in an unlocked condition, means for rotatably connecting said link arm to said pin member and means for locking each sliding member at any selective position along said guide channel, whereby said link arm is rotatably connected to said sliding member when in a locked condition.

2. A sleep-inducing device as recited in claim 1, wherein each means for connecting said base member to said bed frame is independently vertically and horizontally adjustable.

3. A sleep-inducing device as recited in claim 2, wherein said base member connecting means comprises a generally U-shaped clamping device.

4. A sleep-inducing device according to claim 3, further comprising a generally rectangular frame-like member fitting over the bed spring assembly between the spring assembly and the bed mattress and being adapted for receiving the upper portion of the spring assembly and engaging the four sides thereof, said frame-like member further including means to connect said link arm at selective points along the longitudinal length thereof.

5. A sleep-inducing device according to claim 4, wherein said frame-like member further includes means for connecting said link arm to the foot or head of said frame-like members.

6. A sleep-inducing device as recited in claim 4, wherein said bed is a hospital bed having segments lying along the longitudinal axis of said bed and said rectangular frame-like member is adapted to fit over any of said spring segments.

7. A sleep-inducing device according to claim 6, further including means for connecting said frame-like member to said link arm to accommodate the presence of a guard rail on said hospital bed.

8. A sleep-inducing device according to claim 7, further comprising a detachable stand upon which said sleep-inducing device rests to provide elevation necessary for attachment of the device to said hospital bed.

9. A sleep-inducing device according to claim 8, further comprising a decorative cabinet for enclosing said device.

* * * * *